United States Patent [19]
Mitoh et al.

[11] Patent Number: 6,040,196
[45] Date of Patent: *Mar. 21, 2000

[54] METHOD OF EVALUATING A TESTING ELEMENT FOR ANTIGENS OR ANTIBODIES

[75] Inventors: Ayumi Mitoh; Tsuneo Hiraide, both of Tokyo, Japan

[73] Assignee: Asahi Kogaku Kogyo Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/754,647

[22] Filed: Nov. 21, 1996

[30] Foreign Application Priority Data

Nov. 21, 1995 [JP] Japan ..................................... 7-302697

[51] Int. Cl.$^7$ ........................ G01N 33/543; G01N 21/00; G01N 33/53; A61L 5/103
[52] U.S. Cl. .............................. 436/518; 422/55; 422/56; 422/57; 422/58; 422/59; 422/60; 427/2.11; 435/7.92; 435/7.93; 435/7.94; 435/7.95; 435/810; 435/970; 436/518; 436/523; 436/524; 436/525; 436/810
[58] Field of Search ....................... 422/55–60; 427/2.11; 435/7.92–7.95, 810, 970; 436/518, 523, 524, 525, 810

[56] References Cited

U.S. PATENT DOCUMENTS

| Re. 35,267 | 6/1996 | Tsuru et al. .............................. 210/692 |
| 4,119,709 | 10/1978 | Holub ....................................... 436/500 |
| 4,952,323 | 8/1990 | Nakabayashi et al. . |
| 5,030,611 | 7/1991 | Ogawa et al. . |
| 5,039,408 | 8/1991 | Ichitsuka et al. . |
| 5,158,756 | 10/1992 | Ogawa et al. . |
| 5,540,995 | 7/1996 | Kitano et al. ............................ 428/407 |
| 5,597,619 | 1/1997 | Tsuru ....................................... 427/244 |
| 5,599,792 | 2/1997 | Kronis et al. ............................ 514/12 |
| 5,851,670 | 12/1998 | Mitoh et al. ............................ 428/403 |

FOREIGN PATENT DOCUMENTS

| 0420053 | 4/1991 | European Pat. Off. . |
| 6214706 | of 0000 | Japan . |
| 64-38658 | 2/1989 | Japan . |
| 1126554 | 5/1989 | Japan . |
| 1291162 | 11/1989 | Japan . |
| 7174762 | 7/1995 | Japan . |
| 7194970 | 8/1995 | Japan . |
| 2282548 | 4/1995 | United Kingdom . |
| 2293009 | 3/1996 | United Kingdom . |
| 8808534 | 11/1988 | WIPO . |

OTHER PUBLICATIONS

Wecksler et al., "An Hydroxyapatite Batch Assay for the Quantitation of 1.alpha., 25–Dihydroxyvitamin D.sub.3–Receptor Complexes," Analytical Biochemistry, 92:314–323, 1979.

WPI Abstract Accession No. 90–011192/02 of: JP 010291162 A, published Nov. 22, 1989.

WPI Abstract Accession No. 89–188466/26 of: JP 01026554 A, published May 18, 1989.

WPI Abstract Accession No. 89–088902/12 of: JP1038658, published Feb. 8, 1989.

WPI Abstract Accession No. 89–088903/12 of: JP 1038657; published Feb. 8, 1989.

Sigma Chemical Company, "Biochemicals Organic Compounds for Research and Diagnostic Reagents", pp. 2210–2221, published 1993.

*Primary Examiner*—James C. Housel
*Assistant Examiner*—Ja-Na A. Hines
*Attorney, Agent, or Firm*—Greenblum & Bernstein P.L.C.

[57] ABSTRACT

An evaluating method of a testing element having an immobilized antigen or antibody on an immobilizing carrier thereof, which immobilized antigen or antibody has yet to react with another antigen or antibody, which involves contacting the testing element with a solution containing an antibody or antigen reactive with the immobilized antigen or antibody, specifically binding a labelling compound to the reactive antibody or antigen to thereby cause a color-developing reaction of the labelling compound, and determining an amount of the antigen or antibody immobilized on the testing element as a function of a level of produced color. Using this evaluation method, a quantitative determination of the immobilized antigen or antibody can be carried out, and thus the performance of the testing element for antigens or antibodies can be evaluated.

20 Claims, No Drawings

METHOD OF EVALUATING A TESTING ELEMENT FOR ANTIGENS OR ANTIBODIES

BACKGROUND OF THE INVENTION

1. Field of the Invention

The present invention relates to a method of evaluating a testing element for antigens or antibodies, more particularly, the present invention relates to a method of evaluating the performance of a testing element which contains a known antigen or antibody immobilized thereon and is used in a diagnosis of a variety of infectious diseases based on an antigen-antibody reaction.

2. Description of the Related Art

Various types of testing elements such as testing beads, testing sheets and others which comprise an immobilized antigen or antibody of the known type have been provided for use in detecting an antigen or antibody in a biological fluid such as saliva, blood, lymph, excreta and other fluids. Many of the well-known testing elements contain an antigen or antibody immobilized thereon by an adsorption action of the carrier used. However, in these testing elements, it is difficult to always obtain a constant adhesion and thus immobilization of the antigen or antibody to the elements. When the amount of the immobilized antigen or antibody is varied, it becomes necessary to evaluate the quantity of immobilized antigen or antibody and evaluate the performance of the testing element.

SUMMARY OF THE INVENTION

The object of the present invention is to provide an evaluation method for testing elements with immobilized antigen or antibody, which can easily determine the quantity of the immobilized antigen or antibody and also can stably evaluate the functions of the testing elements.

According to the present invention, there is provided a method of evaluating a testing element having an immobilized antigen or antibody on an immobilizing carrier thereof, which comprises the steps of:

contacting the testing element with a solution containing an antibody or antigen reactive with said immobilized antigen or antibody, specifically binding a labelling compound to said reactive antibody or antigen to thereby cause a color-developing reaction of said labelling compound, and determining an amount of the antigen or antibody immobilized on said testing element by determining the level of the produced color.

Using the evaluation method of the present invention, it becomes possible to easily carry out a quantitative determination of the antigen or antibody immobilized on a carrier of the testing element with reference to the color-developing reaction of the labelling compound used, and also stably evaluate the functions and characteristics of the testing element for the antigens or antibodies.

The present disclosure relates to subject matter contained in Japanese patent application No. 7-302697 (filed on Nov. 21, 1995) which is expressly incorporated herein by reference in its entirety.

DESCRIPTION OF THE PREFERRED EMBODIMENTS

In the practice of the present invention, as mentioned above, there is used a testing element having an immobilized antigen or antibody on an immobilizing carrier. The testing element may be formed from a wide variety of immobilizing carriers by fixing an antigen or antibody to the selected immobilizing carrier. Typical examples of a suitable testing element, although they are not restricted to the below mentioned, include:

1. A testing element in the form of detection beads comprising particles of a calcium phosphate compound having a Ca/P ratio of about 1.0 to 2.0 and an average particle diameter of about 1 to 10000 microns, as an immobilizing carrier, having immobilized thereon an antigen or antibody.

2. A testing element in the form of detection sheets comprising a fibrous aggregate with the carried particles of a calcium phosphate compound, as an immobilizing carrier, having immobilized thereon an antigen or antibody. Preferably, the calcium phosphate compound used herein has a Ca/P ratio of about 1.0 to 2.0 and an average particle diameter of about 0.01 to 200 microns. The testing element is preferably in the form of detection sheets for antigens or antibodies. See, for example, Japanese Patent Application No. 6-214706.

3. A testing element in the form of detection beads comprising a granular composite of polymer comprising polymeric granules having coated on a surface thereof a calcium phosphate compound, at least a part of particles of said calcium phosphate compound being penetrated in said polymeric granules, as an immobilizing carrier, having immobilized thereon an antigen or antibody. Preferably, the calcium phosphate compound used herein has a Ca/P ratio of about 1.0 to 2.0. The granular composite of polymer used herein is disclosed in, for example, Japanese Unexamined Patent Publication (Kokai) No. 7-194970.

In view of the above, each particle of the calcium phosphate compound is partially penetrated into one of the polymeric granules.

4. A testing element in the form of detection beads comprising a granular composite of polymer comprising polymeric granules having coated on a surface thereof a calcium phosphate compound, said polymeric granules or said granular composite being dyed, as an immobilizing carrier, having immobilized thereon an antigen or antibody. Preferably, the calcium phosphate compound used herein has a Ca/P ratio of about 1.0 to 2.0. This type of testing element is disclosed in, for example, Japanese Unexamined Patent Publication (Kokai) No. 7-174762.

In the present testing element, when the calcium phosphate compound is used as an immobilizing medium for antigens or antibodies, the calcium phosphate compound used herein is not restrictive, and suitable calcium phosphate compounds include a wide variety of calcium phosphate compounds having a Ca/P ratio in the range of about 1.0 to 2.0. For example, one or more of $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca(PO_3)_2$, $Ca_4O(PO_4)_2$, and $CaHPO_4$ may be used as the calcium phosphate compound. Among these calcium phosphate compounds, the most preferred one is a calcium phosphate compound which contains hydroxyapatite as a principal component thereof. These calcium phosphate compounds may be produced by any conventional method including a wet process, a dry process and other processes.

The particles of the calcium phosphate compound used herein can be produced by using any conventional granulation methods. For example, they can be produced by spray-drying a slurry of the calcium phosphate compound and then calcining the dried product to obtain the intended particles of the calcium phosphate compound. Preferably, sieve and other separation means may be used to select the particles of the calcium phosphate compound having a predetermined range of particle size depending on the intended use of the particles.

The calcium phosphate compound has an excellent adsorption function with respect to antigens or antibodies such as bacteria, viruses and others. However, in order to ensure an immobilization of the antigens or antibodies thereon, it is preferred that after adsorption of the antigens or antibodies on the calcium phosphate compound, the adsorbed antigens or antibodies are further treated with a cross-linking agent such as glutaraldehyde and the like, a binding agent such as formaldehyde, silane coupling agent and the like, or osmium tetrachloride. Examples of suitable silane coupling agents include 3-glycidoxypropyl trimethoxysilane, 3-thiopropyl trimethoxysilane, 2-(3-trimethoxysilylpropyldithio)-5-nitropyridine, 3-aminopropyl triethoxysilane, 3-chloropropyl dimethoxymethylsilane and the like. Thus, the immobilized antigen or antibody has yet to react with another antigen or antibody.

After immobilization, it is preferred that antigen- or antibody-unadsorbed sites of the immobilizing carrier are treated with a blocking agent. The blocking agent used herein is not restricted, insofar as it is able to be adsorbed on said unadsorbed sites of the calcium phosphate compound and does not adversely affect the subsequently caused antigen-antibody reaction. Suitable blocking agents include, for example, proteins such as casein and albumin.

The evaluation method of the testing element according to the present invention, as mentioned above, comprises the steps of:

contacting the testing element with a solution containing an antibody or antigen reactive with said immobilized antigen or antibody, specifically binding a labelling compound to said reactive antibody or antigen to thereby cause a color-developing reaction of said labelling compound, and determining an amount of the antigen or antibody immobilized on said testing element by determining the level of the produced color.

Preferably, the testing element is contacted with a solution containing a known amount of antibody or antigen reactive with said immobilized antigen or antibody.

In the practice of the present evaluation method, preferably, an antibody or antigen reactive with an immobilized antigen or antibody is separately prepared, and then diluted with a solvent to prepare a series of the diluted solution of antibody or antigen with different dilution degree. Suitable solvents useful in the preparation of the diluted solution include, for example, physiological saline, phosphate buffer solution (PBS) and the like. Then, the resulting solution of antigen or antibody is contacted with a testing element containing an immobilized antigen or immobilized antibody to be evaluated, to thereby cause an antigen-antibody reaction. The thus formed composite of antigen and antibody is then labelled with a labelling compound capable of specifically binding to said composite, thereby generating a color-developing reaction of the labelling compound. The color-developing reaction thus generated can be utilized as a quantitative measure of said immobilized antigen or immobilized antibody.

The evaluation of the testing element can be carried out as follows.

Distinct portions of a reference testing element having a standard amount of an immobilized antigen or antibody are contacted with a series of the diluted solution of a known amount of antibody or antigen with different dilution degree to produce an antigen-antibody composite, and then, contacted with a labelling compound capable of generating a color-developing reaction with said antigen-antibody composite. The so developed color is used as reference.

Separately, distinct portions of the testing element to be evaluated, to which an unknown amount of an antigen or antibody is immobilized, are contacted with the same series of the diluted solution of the antigen or antibody as above and then, contacted with the same labelling compound as above. The density of the developed color is compared with the density of reference color.

When the testing element to be evaluated shows the same color density as that of the reference testing element, both elements have the same amount of immobilized antigen or antibody. Accordingly, the amount of the antigen or antibody immobilized on the testing element to be evaluated can be determined from the dilution degree of the used solution of the antibody or antigen when the same color density is developed.

In view of the above, it is evident that the present invention may be conducted during or subsequent to the manufacture of the testing element. Further, the present invention may be directed to a quality control method.

The labelling compound used herein is not restrictive, insofar as it may specifically bind to the antibody or antigen which has been reacted with the immobilized antigen or immobilized antibody. Suitable labelling compounds, although they are not restricted to the below-mentioned, include, antigens or antibodies conjugated to peroxidase, glucose oxidase, tyrosinase, acidic phosphatase or alkaline phosphatase as a labelling enzyme.

Using the above-listed labelling enzymes, it becomes easy to induce the subsequent color-developing reaction and thus the quantitative determination of the amount of the antigen or antibody immobilized on the carrier. Namely, the color developing reaction can be easily induced by using a substrate which can be labelled with an enzyme and can develop a color upon reaction with said enzyme.

The substrate advantageously used herein includes, for example, substrates for dyeing immune tissues such as True Blue (trade name) commercially available from Kirkegaard Laboratories, Inc. and containing 3,3',5,5'-tetramethylbenzidine and hydrogen peroxide, DAB (3,3'-diaminobenzide) and the like.

The present invention will be further described with reference to working examples thereof. Note, however, that the present invention should not be restricted to these examples.

EXAMPLE 1

Preparation of Immobilizing Carrier 50 g of beads of polymethylmethacrylate (PMMA) having an average granule diameter of 7 microns and a density of 1.19 g/cm$^3$, dyed with a quinophthalone disperse dye, MITSUI ML Colors ML Yellow VF-2 (trade name) commercially available from Mitsui Toatsu Senryo Kabushiki Kaisha, and 5.0 g of particules of calcium phosphate compound having a Ca/P ratio of 1.5, average particle diameter of 2 microns, specific surface area of 12 m$^2$/g, apparent density of 2.4 g/cm$^3$ and pore size of 1000 angstroms were blended at 38 to 71° C. for 5 minutes in a Nara Hybridization System NHS-1 (commercially available from Nara Kikai Seisakusho; rated power: 5.5 kw and rated current: 23 A) rotated at 8000 rpm to produce PMMA beads having a coating of calcium phosphate compound applied over a surface of the beads. The resulting coating of calcium phosphate compound had an average thickness of 0.27 microns. The resulting granular composite had an average granule diameter of 7.5 microns, density of 1.3 g/cm³ and pore size of 1000 angstroms, and showed a pale yellow color.

Preparation of Testing Element

An antigen for Japanese encephalitis strain Nakayama vaccine was adsorbed on the granular composite obtained in the above step, and centrifuged to remove the excess antigen. Then, the antigen adsorbed on the composite was immobilized by immersing the composite in a solution of 0.1% by weight of glutaraldehyde. After immobilization of the antigen, the composite was immersed in a solution of a blocking agent containing casein, trade name "Block Ace" commercially available from Snow Brands Milk Products Co., Ltd. After thorough stirring, the solution was centrifuged to remove the excess blocking agent. Composite beads having immobilized thereon an antigen for the strain Nakayama vaccine were thus produced.

Evaluation of Testing Element 100 microliters of a phosphate buffer solution (PBS) containing 0.5 w/v % of the composite beads with the immobilized antigen for the strain Nakayama vaccine was added to a test tube. Then, 100 microliters of a rabbit antiserum to said strain Nakayama vaccine was added to the test tube, after said rabbit antiserum was diluted with doubling to make a dilution degree of from 500 times to 32000 times. The mixture was shaken at room temperature for 45 minutes. After addition of PBS, the mixture was centrifuged at 1500 rpm for 5 minutes to separate a supernatant to thereby remove unreacted antibody.

Thereafter, 500 microliters of 500 times-diluted anti-rabbit IgG peroxidase labelling antibody was added to each of the test tubes and shaken at room temperature for one hour. After centrifugal washing, 50 microliters of a substrate for dyeing immune tissues, True Blue (trade name) commercially available from Kirkegaard Laboratories, Inc., was added to the test tube, and after one minute, water was added to the test tube to stop the reaction therein. It was found from the observation of the coloring of the beads in the test tube that a certain level or density of the coloring (bluish green) could be obtained for the dilution degree of the antiserum of from 500 times to 4000 times, and the coloring could be weakened with increase of the dilution degree, and that such clear variation of the coloring could be observed until the dilution degree is increased to 16000 times, in comparison with the control containing no antiserum. The above results are evidence that the described detection method enables the visual determination of an amount of the immobilized antigen or antibody on the strain Nakayama vaccine antigen-immobilized composite beads.

EXAMPLE 2

Preparation of Immobilizing Carrier 50 g of nylon beads having an average granule diameter of 5 microns and a density of 1.03 $g/cm^3$, dyed with an anthraquinone disperse dye, MITSUI ML Colors ML Red VF-2 (trade name) commercially available from Mitsui Toatsu Senryo Kabushiki Kaisha, and 7.5 g of particles of hydroxyapatite having a Ca/P ratio of 1.67, average particle diameter of 5 microns, specific surface area of 45 $m^2/g$, apparent density of 1.8 $g/cm^3$ and pore size of 600 angstroms were blended at 32 to 50° C. for 5 minutes in a Nara Hybridization System NHS-1 (commercially available from Nara Kikai Seisakusho; rated power: 5.5 kw and rated current: 23 A) at a rotation speed of 8000 rpm to produce nylon beads having a coating of hydroxyapatite applied over a surface of the beads. The resulting coating of hydroxyapatite had a thickness of 0.44 microns on average. The resulting granular composite had an average granule diameter of 5.8 microns, density of 1.13 $g/cm^3$ and pore size of 600 angstroms, and showed a pink color.

Preparation of Testing Element

The procedure of Example 1 was repeated with the proviso that an antigen of A-type influenza virus was adsorbed on the granular composite in place of the antigen of Japanese encephalitis strain Nakayama vaccine. The composite beads having immobilized thereon an antigen for the influenza virus were thus produced.

Evaluation of Testing Element 50 microliters of a phosphate buffer solution (PBS) containing 0.5 w/v % of the composite beads with the immobilized antigen for the influenza virus was poured into each of 96 wells having a V-shaped bottom in a microplate. Then, 50 microliters of a rabbit antiserum to said influenza virus and of a rabbit antiserum to other viruses were added to the wells of the microplate, after said rabbit antiserums were diluted to make different concentrations. The microplate was shaken at room temperature for one hour. After this treatment of the composite beads, PBS was added, and the centrifugal washing was repeated twice.

Thereafter, 50 microliters of 500 times-diluted anti-rabbit IgG peroxidase labelling antibody was added to each of the wells. The microplate was shaken at room temperature for one hour, and centrifugally washed with PBS. Then, 25 microliters of a substrate for dyeing immune tissues, True Blue (trade name) was added to each well, and after one minute, water was added to the well to stop the reaction therein. It was found from the observation of the coloring of the beads in the wells that all the test elements could not develop a color for the wells containing a rabbit antiserum to the virus other than influenza virus, while the coloring (purple) could be obtained for the wells containing a rabbit antiserum to the influenza virus until a dilution degree of 10000 times. The above results evidence that the described evaluation method enables evaluation with remarkably high sensitivity.

EXAMPLE 3

Preparation of Immobilizing Carrier 50 g of nylon beads having an average granule diameter of 5 microns and a density of 1.02 $g/cm^3$ and 7.5 g of particles of hydroxyapatite having a Ca/P ratio of 1.67, average particle diameter of 5 microns, specific surface area of 45 $m^2/g$, apparent density of 1.8 $g/cm^3$ and pore size of 600 angstroms were blended at 34 to 47° C. for 5 minutes in a Nara Hybridization System NHS-1 (commercially available from Nara Kikai Seisakusho; rated power: 5.5 kw and rated current: 23 A) at a rotation speed of 8000 rpm to produce nylon beads having a coating of hydroxyapatite applied over a surface of the beads. The resulting coating of hydroxyapatite had a thickness of 0.45 microns on average. The resulting granular composite had an average granule diameter of 5.8 microns, density of 1.12 $g/cm^3$ and pore size of 600 angstroms.

Preparation of Testing Element

The procedure of Example 1 was repeated to produce the composite beads having immobilized thereon an antigen for the Japanese encephalitis strain Nakayama vaccine.

Evaluation of Testing Element 100 microliters of a phosphate buffer solution (PBS) containing 0.5 w/v % of the composite beads with the immobilized antigen for the strain Nakayama vaccine was added to a test tube. Then, 100 microliters of a rabbit antiserum to said strain Nakayama vaccine was added to the test tube, after said rabbit antiserum was diluted with doubling to make a dilution degree of from 500 times to 32000 times. The test tube was shaken at room temperature for 45 minutes. After addition of PBS, the mixture was centrifuged at 1500 rpm for 5 minutes to separate a supernatant to thereby remove an unreacted antibody.

Thereafter, 500 microliters of 500 times-diluted anti-rabbit IgG peroxidase labelling antibody was added to each of the test tubes and shaken at room temperature for one hour. After centrifugal washing, 50 microliters of a substrate for dyeing immune tissues, True Blue (trade name) was added to the test tube, and after one minute, water was added to the test tube to stop the reaction therein. It was found from the observation of the coloring of the beads in the test tube that a certain level or density of the coloring (blue) could be obtained for the dilution degree of the antiserum of from 500 times to 4000 times, and the coloring could be weakened with increase of the dilution degree, and that such clear variation of the coloring could be observed until the dilution degree was increased to 16000 times, in comparison with the control containing no antiserum. The above results are evidence that the described detection method enables the visual determination of an amount of the immobilized antigen or antibody on the strain Nakayama vaccine antigen-immobilized composite beads.

EXAMPLE 4
Preparation of Testing Element

The procedure of Example 1 was repeated with the proviso that porous granules of hydroxyapatite having a grain diameter of 300 to 600 microns (average grain diameter of 450 microns), pore size of 0.005 to 0.01 microns and specific surface area of 10 $m^2/g$ were used as the immobilizing carrier in place of the granular colored composite having an average granule diameter of 7.5 microns, density of 1.3 $g/cm^3$ and pore size of 1000 angstroms. The hydroxyapatite beads having immobilized thereon an antigen for the Japanese encephalitis strain Nakayama vaccine were thus produced.

Evaluation of Testing Element 100 microliters of a phosphate buffer solution (PBS) containing 0.5 w/v % of the hydroxyapatite beads with the immobilized antigen for the strain Nakayama vaccine was added to a test tube. Then, 100 microliters of a rabbit antiserum to said strain Nakayama vaccine was added to the test tube, after said rabbit antiserum was diluted with doubling to make a dilution degree of from 500 times to 32000 times. The test tube was shaken at room temperature for 45 minutes. After addition of PBS, the mixture was centrifuged at 1500 rpm for 3 minutes to separate a supernatant to thereby remove an unreacted antibody.

Thereafter, 500 microliters of 500 times-diluted anti-rabbit IgG peroxidase labelling antibody was added to each of the test tubes and shaken at room temperature for one hour. After centrifugal washing, 50 microliters of a substrate for dyeing immune tissues, True Blue (trade name) was added to the test tube, and after one minute, water was added to the test tube to stop the reaction therein. It was found from the observation of the coloring of the beads in the test tube that a certain level or density of the coloring (blue) could be obtained for the dilution degree of the antiserum of from 500 times to 4000 times, and the coloring could be weakened by increasing the dilution degree, and that such clear variation of the coloring could be observed until the dilution degree was increased to 16000 times. The above results are evidence that the described detection method enables the visual determination of an amount of the immobilized antigen or antibody on the strain Nakayama vaccine antigen-immobilized hydroxyapatite beads.

EXAMPLE 5
Preparation of Immobilizing Carrier

Porous granules of hydroxyapatite having an average grain diameter of 3.5 microns and a Ca/P ratio of 1.67 were applied to a nonwoven fabric having a thickness of 0.2 mm and a size of 5 mm×10 mm consisting of 50% by weight of polyethylene and 50% by weight of polyethylene terephthalate ester, followed by thermal treatment to produce a ceramics-carried fibrous composite having substantially uniformly carried thereon 24% by weight of the hydroxyapatite granules.

Preparation of Testing Element

A 256 HA (hemagglutination) value of A-type influenza virus was absorbed onto the fibrous composite, and then immobilized on the composite by immersing the composite in a solution of 0.05% by weight of glutaraldehyde. After immobilization of the influenza virus, the fibrous composite was immersed in a four times-diluted solution of a blocking agent containing casein, Block Ace (trade name), to selectively mask the influenza virus-unadsorbed sites of the composite. The fibrous composite was again treated with a solution of 0.05% by weight of glutaraldehydethe to immobilize said blocking agent. Further, the fibrous composite was immersed in a neutral buffer solution containing the blocking agent to inactivate an aldehyde residue remaining on the composite as a function of the chemical bonding between the aldehyde residue and proteins. The influenza virus-bonded fibrous composite as the testing element was thus produced.

Evaluation of Testing Element

The resulting influenza virus-bonded fibrous composite was added to test tubes each of which contains a diluted rabbit antiserum to said influenza virus or a diluted rabbit antiserum to other viruses in different concentrations. The mixture in the test tube was shaken at room temperature for one hour. After washing with PBS, 500 microliters of 500 times-diluted anti-rabbit IgG peroxidase labelling antibody was added to each of the test tubes, and shaken at room temperature for one hour. After centrifugal washing with PBS, 200 microliters of a substrate for dyeing immune tissues, True Blue (trade name), was added to the test tube, and after one minute, water was added to the test tube to stop the reaction therein. It was found from the observation of the coloring of the fibrous composite in the test tube that all the test elements could not develop a color for the test tubes containing a rabbit antiserum to the virus other than the influenza virus, while the coloring (purple) could be obtained for the test tubes containing a rabit antiserum to the influenza virus until a dilution degree of 10000 times. The above results are evidence that the described evaluation method enables evaluation with remarkably high sensitivity.

We claim:

1. A method of evaluating an amount of antigen or antibody immobilized on a solid phase carrier comprising a calcium phosphate compound, of a test element, the method comprising:
   (a) contacting the test element with a known amount of a first antibody or antigen which specifically binds to the immobilized antigen or antibody, respectively, to form a first immunocomplex;
   (b) contacting the first immunocomplex with an enzyme-labelled antigen or antibody which specifically binds to the first antibody or antigen to form a labelled immunocomplex;
   (c) contacting the labelled immunocomplex with a substrate which reacts with the enzyme of the enzyme-labelled antigen or antibody to produce a color; and (d) comparing the amount of the color produced on the test element to a standard color produced by a reference test element with a known amount of the immobilized antigen or antibody thereon processed according to (a)–(c) to determine the amount of the antigen or antibody immobilized on the solid phase carrier of the test element.

2. The method of claim 1, wherein the evaluation of the test element and the comparing occurs during manufacture of the test element.

3. The method of claim 1, wherein prior to evaluation of the amount of antigen or antibody immobilized on the solid phase carrier, the immobilized antigen or antibody has yet to react with another antigen or antibody.

4. The method of claim 1, wherein the solid phase carrier comprises particles of a calcium phosphate compound having a calcium to phosphorus ratio of about 1.0 to 2.0 and an average particle diameter of about 1 to 10,000 microns.

5. The method of claim 1, wherein the solid phase carrier comprises a fibrous aggregate with carried particles of a calcium phosphate compound having an average particle diameter of about 0.01 to 200 microns and a calcium to phosphorus ratio of about 1.0 to 2.0.

6. The method of claim 1, wherein the solid phase carrier comprises a granular composite comprising polymeric granules having coated on a surface thereof a calcium phosphate compound having a calcium to phosphorus ratio of about 1.0 to 2.0, wherein each particle of the calcium phosphate compound is partially penetrated into one of the polymeric granules.

7. The method of claim 1, wherein the solid phase carrier comprises a granular composite comprising polymeric granules having coated on a surface thereof a calcium phosphate compound having a calcium to phosphorus ratio of about 1.0 to 2.0, at least one of the polymeric granules and the granular composite being dyed.

8. The method of claim 1, wherein the enzyme of the enzyme-labelled antigen or antibody comprises an enzyme selected from the group consisting of peroxidase, glucose oxidase, tyrosinase, acidic phosphatase, and alkaline phosphatase.

9. The method of claim 1, wherein distinct portions of the reference testing element are contacted with a series of diluted solutions of a known amount of antigen or antibody with different dilution degree, and wherein the reference testing element comprises a solid phase carrier including a calcium phosphate compound.

10. The method of claim 9, wherein contacting the testing element comprises contacting distinct portions of the testing element with the series of diluted solutions.

11. A method of evaluating an amount of antigen or antibody immobilized on a solid phase carrier comprising a calcium phosphate compound, of a test element, the method comprising:

(a) contacting the test element with a known amount of a first antibody or antigen which specifically binds to the immobilized antigen or antibody, respectively, to form a first immunocomplex;

(b) contacting the first immunocomplex with a labelled antigen or antibody which specifically binds to the first antibody or antigen to form a labelled immunocomplex; and (c) comparing the test element having the labelled immunocomplex with a reference test element with a known amount of the immobilized antigen or antibody thereon processed according to (a)–(b) to determine the amount of the antigen or antibody immobilized on the solid phase carrier of the test element.

12. The method of claim 11, wherein the evaluation of the test element and the comparing occur during manufacture of the test element.

13. The method of claim 11, wherein prior to evaluation of the amount of antigen or antibody immobilized on the solid phase carrier, the immobilized antigen or antibody has yet to react with another antigen or antibody.

14. The method of claim 11, wherein distinct portions of the reference testing element are contacted with a series of diluted solutions of a known amount of antigen or antibody with different dilution degree, and wherein the reference testing element comprises a solid phase carrier including a calcium phosphate compound.

15. The method of claim 14, wherein contacting the testing element comprises contacting distinct portions of the testing element with the series of diluted solutions.

16. A quality control method of evaluating an amount of antigen or antibody immobilized on a solid phase carrier comprising a calcium phosphate compound, of a test element, the method comprising:

(a) contacting the test element with a known amount of a first antibody or antigen which specifically binds to the immobilized antigen or antibody, respectively, to form a first immunocomplex;

(b) contacting the first immunocomplex with a labelled antigen or antibody which specifically binds to the first antibody or antigen to form a labelled immunocomplex; and (c) comparing the test element having the labelled immunocomplex with a reference test element with a known amount of the immobilized antigen or antibody thereon processed according to (a)–(b) to determine the amount of the antigen or antibody immobilized on the solid phase carrier of the test element.

17. The quality control method of claim 16, wherein the labelled antigen or antibody comprises an enzyme-labelled antigen or antibody, and wherein (b) further comprises contacting the labelled immunocomplex with a substrate which reacts with the enzyme of the enzyme-labelled antigen or antibody to produce a color, and wherein (c) comprises comparing the amount of the color produced to a standard color produced by a reference test element with a known amount of the immobilized antigen or antibody thereon processed according to (a)–(b) to determine the amount of the antigen or antibody immobilized on the solid phase carrier of the test element.

18. The quality control method of claim 16, wherein the evaluation of the test element and the comparing occurs during manufacture of the test element.

19. The quality control method of claim 16, wherein prior to evaluation of the amount of antigen or antibody immobilized on the solid phase carrier, the immobilized antigen or antibody has yet to react with another antigen or antibody.

20. The quality control method of claim 16, wherein distinct portions of the reference testing element are contacted with a series of diluted solutions of a known amount of antigen or antibody with different dilution degree, and wherein the reference testing element comprises a solid phase carrier including a calcium phosphate compound.

* * * * *